United States Patent [19]

Sakaguchi

[11] 4,331,765

[45] May 25, 1982

[54] **METHOD OF DEODORIZING *HOUTTUYNIA CORDATA* THUNB**

[76] Inventor: Hiroshi Sakaguchi, c/o Takanoha Apt., No. 1-8-11, Nishikata, Bunkyo-ku, Tokyo, Japan

[21] Appl. No.: 193,646

[22] Filed: Oct. 3, 1980

[30] Foreign Application Priority Data

Aug. 27, 1980 [JP] Japan .................................. 55/118140

[51] Int. Cl.³ ............................................. C07G 17/00
[52] U.S. Cl. .................................... 435/267; 435/170; 435/171; 435/253; 435/255
[58] Field of Search ............... 435/267, 253, 170, 171, 435/254, 255

[56] References Cited

U.S. PATENT DOCUMENTS

| | | | |
|---|---|---|---|
| 3,460,950 | 8/1969 | Fujita et al. | 435/267 X |
| 3,833,472 | 9/1974 | Yamauchi | 435/267 X |
| 3,878,050 | 4/1975 | Lee | 435/253 X |
| 3,893,889 | 7/1975 | Warren et al. | 435/253 X |
| 4,204,043 | 5/1980 | Schultz | 435/267 |

*Primary Examiner*—Robert J. Warden
*Attorney, Agent, or Firm*—Jacobs & Jacobs

[57] ABSTRACT

*Houttuynia cordata* Thunb, a medical herb, has an inherent odor due to lauric aldehyde and homologs thereof contained therein. This invention provides a method of removing said inherent odor from *Houttuynia cordata* Thunb which comprises subjecting green *Houttuynia cordata* Thunb to a heat-treatment and then fermenting the thus heat-treated *Houttuynia cordata* Thunb with yeast, koji or a mixture thereof inoculated therein.

8 Claims, No Drawings

METHOD OF DEODORIZING *HOUTTUYNIA CORDATA* THUNB

BACKGROUND OF THE INVENTION

This invention relates to a method of removing the inherent odor from *Houttuynia cordata* Thunb, and more particularly to a method of deodorizing *Houttuynia cordata* Thunb in which a heat-treatment and a fermentation are combined.

*Houttuynia cordata* Thunb, which has an inherent odor, has been widely known as Herb Houttuyniae from ancient times. The excellent medicinal effects thereof have been described in various publications relating to herb medicines.

For popular internal use, *Houttuynia cordata* Thunb is taken as a juice obtained from green leaves thereof or a decoction of a dried product of *Houttuynia cordata* Thunb collected before the flowering time thereof.

Although *Houttuynia cordata* Thunb has the aforementioned excellent medicinal effects and is established as an innocuous popular medicine, the untreated product thereof is difficult to drink due to its inherent odor and has poor storage stability. Additionally, the period of its utilization is limited to the growing period thereof.

The odor can be removed therefrom by drying in the shade, but the product thus dried must be decocted for a long time until the medicinal components are sufficiently extracted therefrom, which proves to be quite inconvenient.

It is well known that the inherent odor of *Houttuynia cordata* Thunb is due to lauric aldehyde, $C_{11}H_{23}CHO$, or its homologs, and is also known that these compounds can be removed by steam distillation.

Under these circumstances, the inventor found that the inherent odor of *Houttuynia cordata* Thunb can be removed therefrom by mashing or crushing green *Houttuynia cordata* Thunb and then fermenting the thus crushed matter with yeast inoculated therein.

However, since the aforementioned method allows easy contamination of the material, the final product may contain undesirable by-products derived from the contamination. When no additive is used, the final product may be unacceptable for internal use if such by-products are contained therein and in the past the product has often been discarded. If a germicidal agent or the like is used in the washing medium to remove sundry germs, the final product may contain undesirable impurities. Additionally, for the prevention of the entry of sundry germs, sterilizers or the like into the material, it is necessary in using said method to completely remove the wash water therefrom by letting the material dry or to wiping it completely after washing. This introduces troublesome operations.

SUMMARY OF THE INVENTION

One method for overcoming the aforementioned disadvantages is to subject green *Houttuynia cordata* Thunb, directly or after crushing, to a heat-treatment.

Accordingly it is an object of the present invention to provide a method of removing the inherent odor from *Houttuynia cordata* Thunb, thereby making it easy to drink.

It is another object of the present invention to provide a method of deodorizing *Houttuynia cordata* Thunb which is safe against the contamination of the final product by undesirable by-products produced by sundry germs contained in the starting material.

It is another object of the present invention to provide a method of deodorizing *Houttuynia cordata* Thunb to give a product having good storage stability which is available throughout the year regardless of the growing period of the medical herb.

Other objects and features of the present invention will become apparent from the following description.

The present invention relates to a method of deodorizing *Houttuynia cordata* Thunb which comprises heating green *Houttuynia cordata* Thunb to obtain a liquid material therefrom, fermenting the liquid material as a culture medium with yeast, koji or mixture thereof inoculated therein and then separating the resulting liquid phase and precipitates.

DETAILED DESCRIPTION OF THE INVENTION

The present invention will be more specifically explained hereinafter.

In practice, green *Houttuynia cordata* Thunb is first subjected to a heat-treatment. As heat-treatmet there may be employed any of the conventional heat-treatment means. Examples of suitable heat-treatment means which may be employed in the present invention are steaming by a steaming basket, boiling in an iron pot and treating by a hot-air oven.

The liquid material thus obtained is a dark green-colored viscous liquid emitting a bad smell inherent to *Houttuynia cordata* Thunb. The liquid is then inoculated with yeast, koji or mixture thereof.

As yeast there may be employed any of the commercially-available yeasts or any of the yeasts for use in beer fermentation and sake fermentation.

As koji there may be employed the kojis derived from grains such as rice, bean, barley and the like.

The necessary amount of yeast and/or koji may be determined by the conventional proportion used in the fermentation industry of this field and has no particular limit. In the fermentation industry, the amount of yeast and/or koji may be widely varied depending on various factors such as the fermentation temperature, the fermentation time and the amount of additives. Those skilled in the art have properly combined these factors as well as the amount and the kind of yeast and/or koji to obtain products having subtle differences in their tastes. In practice, however, a cultured yeast liquid in which the population of the strain is equal to about $10^8$ per cc is added to the liquid *Houttuynia cordata* Thunb or its mixture with additives at an approximate volumetric ratio of 1/500.

In addition, as proved by the conventional process employed in the fermentation industry, lees recovered from fermentation product may be employed in place of said yeast and/or koji. Accordingly, it should be understood that the use of said lees falls within the scope of the present invention.

The liquid material (culture medium) thus inoculated separates into a liquid phase and a precipitate phase as the fermentation proceeds. After the material is sufficiently matured, said liquid phase is separated from the other by a proper separating means.

As separating means, there may be employed any of the conventional means, for example filtration, centrifugation, decantation and siphoning.

In the present invention there may be optionally added to said culture medium commonly-used carbon source as additives, such as saccharides, starch syrup, honey, molasses and starch. These additives may be employed independently or in the form of a mixture thereof. The addition thereof to the culture medium may be carried out prior to or during fermentation.

Examples of suitable starch for carbon source which may be employed in the present invention are corn starch, sweet potato starch, potato starch, wheat starch and rice starch.

Additionally, it is to be understood that, aside from the aforementioned carbon source, there may be employed various carbohydrates or any carbon source which may cause alcohol fermentation by the action of yeast and/or koji.

As apparent to those skilled in the art, the proportion of the additives is less than 50% by volume based on the volume of the liquid material, preferably less than 35%.

In the case of fermentation in the presence of additives, the fermentation process is accompanied by the alcohol fermentation of the additives with yeast, thereby providing alcohol in the final product. The presence of alcohol in the final product is extremely significant not only for the effective extraction of active constituents of *Houttuynia cordata* Thunb, such as quercitrin, iso-quercitrin and myrcene, most of which are completely or nearly insoluble in water, but also for the enhancement of the storage stability of the product.

In an alternative embodiment of the present invention, similar effects may be obtained by subjecting green *Houttuynia cordata* Thunb to the heat-treatment after it is crushed or mashed to a liquid material. As crushing means there may be employed any of the conventional means, such as a mixer, mill, crusher, triturator or juicer.

The present invention will be more specifically explained hereinafter referring to the following preferred embodiment.

In practice, *Houttuynia cordata* Thunb is first subjected to steaming in a proper heating apparatus. Herein, water-washing may be effected for the removal of contaminants from the raw material. The material thus steam-treated can be liquefied simply by agitation. At this stage, there may be optionally effected a process for removing the rough dregs, which are composed of fibrous materials, therefrom by filtration or pressing. The liquid material thus obtained is then cooled to a temperature ranging from about 15° to 35° C. A proper amount of yeast and/or koji or lees containing the former is added to the liquid material thus cooled and then stirred. The liquid material thus treated is put in a proper container, e.g. glass bottle, is then fermented while maintaining the temperature in a range of from about 15° to 35° C. by using a proper temperature-regulating system. The fermentation period may vary from about 1 to 15 days or more depending on the fermentation temperature, the amount of yeast and/or koji or lees containing the former, the amount of additives, and so on. (Said fermentation period is a mere illustration and is not an essential factor in the present invention.) Since the cloudy mixture of the liquefied *Houttuynia cordata* Thunb and yeasts separates into a liquid phase and a solid phase (precipitate phase; lees) as fermentation proceeds, the completion of fermentation can be determined with the naked eye. Otherwise, the completion of fermentation may be judged from the condition of bubbling ($CO_2$ and the like) during the fermentation process. After the completion of fermentation, said liquid phase is separated from said precipitate phase by a proper separating means.

The product thus obtained is a clear, reddish or orange-colored liquid quite free of the inherent odor of *Houttuynia cordata* Thunb, which provides various, well-known, excellent medicinal effects.

Said product shows a high storage stability when kept in a cool dark place in a pigmented or colored sealable container, e.g. a brown glass bottle, after being sterilized by a proper heating means. The sterilization treatment may be effected by, for example, heating at 65° C. or more. According to the inventor's experience, said product can stably be preserved for at least 6 years. Furthermore, it was found that the product becomes more excellent in its taste with prolonged preservation.

Heat-treatment, which is the feature of the present invention, makes it possible to obtain the following advantages:

Firstly, the heat-treatment can kill sundry germs attached to or living upon raw *Houttuynia cordata* Thunb, thus preventing the presence of undesirable by-products produced by the action of sundry germs in the final product. Thereby, a product excellent in its taste can be obtained.

Additionally, said heat-treatment can prevent the formation of inferior products due to the propagation of undesirable germs during the fermentation process as in the conventional method, especially in the case of using no additives, thus providing an economical and industrial advantage.

Secondly, said heat-treatment eliminates troublesome processes such as washing and dehydration, and in some embodiments eliminates the need for mashing or crushing process, thus enabling a remarkable simplification of the production process.

In addition, said heat-treatment permits free use of *Houttuynia cordata* Thunb throughout the year regardless of the vegetation period of the material.

Since the lees obtained in the separation process are quite free of the inherent odor of *Houttuynia cordata* Thunb, it can be understood that lauric aldehyde and its homologs, which are the source of the inherent odor of *Houttuynia cordata* Thunb, are completely removed by the method of the present invention.

The theoretical basis for the deodorization of *Houttuynia cordata* Thunb in the present invention is unknown. However, it may be hypothesized that lauric aldehyde and its homologs are decomposed by yeasts or the like or converted to compounds of other kinds by certain reactions accompanying the fermentation.

The present invention is further illustrated by, but not limited by, the following examples:

EXAMPLE 1

Green *Houttuynia cordata* Thunb was subjected to steaming in a steaming basket. The material thus treated was moved into an open container and stirred to obtain a liquid material. The liquid material thus obtained was then cooled to room temperature and there was added thereto a commercially-available liquid yeast at a volumetric mixing ratio of 1/20. The mixture thus obtained was put in a glass bottle and kept at room temperature (about 27° C.) for fermentation. The fermentation was completed in twenty-four hours and it was observed that lees were precipitated to leave a clear liquid phase thereon. Then the content of the bottle was filtered to remove the precipitates and a clear product was obtained. The product thus obtained was a tasteless and odorless brown clear liquid quite free of the inherent odor of *Houttuynia cordata* Thunb. The lees thus separated, also free of said odor, were properly preserved for reuse as yeast.

As compared to the products prepared by the conventional methods, which do not include any heat-treatments, the product prepared in this example, which uses no additives, showed a remarkably improved storage stability and exhibited no sourness.

EXAMPLES 2 TO 8

The present invention was carried out as in Example 1, except that honey or starch syrup was added as additive to the liquid material at one of the volumetric mixing ratios listed below before inoculation with yeast, and as yeast there was employed the lees obtained in Example 1.

| Example No. | Liquefied Houttuynia Cordata Thunb | Honey or Starch Syrup |
| --- | --- | --- |
| 2 | 9/10 | 1/10 |
| 3 | 8/9 | 1/9 |
| 4 | 7/8 | 1/8 |
| 5 | 6/7 | 1/7 |
| 6 | 5/6 | 1/6 |
| 7 | 4/5 | 1/5 |
| 8 | 3/4 | 1/4 |

The fermentation was carried out at room temperature as in Example 1. The period necessary for completion of fermentation varied from 3 to 4 days. In each example two runs were effected one with each of the above kinds of additives, i.e. honey and starch syrup.

All the products prepared in Examples 2 to 8 were reddish or orange-colored liquids free of the inherent odor of *Houttuynia cordata* Thunb and extremely excellent in storage stability.

Example 7 shows the most excellent result; the fermentation was completed in the shortest time (3 days) and the product tasted excellent.

The lees obtained in Examples 2 to 8 were removed and properly preserved for reuse.

EXAMPLE 9

The present invention was carried out as in Example 1, except that as an additive there was employed sugar in a mixing ratio of 200 g/l, based on the liquid material of *Houttuynia cordata* Thunb. As yeast there was employed the lees obtained in Example 1. The result was the same as in the foregoing Examples. The fermentation period was 4 days.

EXAMPLE 10

The present invention was carried out as in Examples 2 to 8, except that as yeast there was employed a cultured yeast liquid in which the population of the strain was equal to about $10^8$ per cc in a mixing ratio of 1/500, based on the culture medium. The fermentation periods were 3 to 4 days. The results were the same as in Examples 2 to 8.

In addition to the above examples, various examples using koji were effected. The results were the same as in the above examples in which yeast was employed.

In the present invention, medical herbs other than *Houttuynia cordata* Thunb such as *Saxifraga stolonifera* Meerburg, *Plantago asiatica* L. and *Lycium chinense* Mill may be employed. In the case of medical herbs which do not have inherent odor, the application of the method of present invention is not so important in the deodorization effect. However, the present invention can convert any of the above medical herbs to a product having good storage stability, thus enabling a free use of the material throughout the year regardless of the vegetation period thereof.

What is claimed is:

1. A method of deodorizing *Houttuynia cordata* Thunb which comprises heating green *Houttuynia cordata* Thunb to obtain a liquified Houttuynia, inoculating the thus obtained liquified Houttuynia as culture medium with yeast, koji or a mixture thereof, and fermenting the thus inoculated liquified Houttuynia.

2. A method as claimed in claim 1, wherein said culture medium contains a carbon source as an additive.

3. A method as claimed in claim 2, wherein said carbon source is selected from the group consisting of saccharides, starch syrup, honey, starch, molasses and mixture thereof.

4. A method as claimed in claim 1, wherein the green *Houttuynia cordata* Thunb is mashed or crushed before being heated.

5. A method as claimed in claim 1, including removing lees precipitated from said fermented liquified Houttuynia.

6. A method as claimed in claim 5, wherein as yeast there is used the precipitated lees.

7. A liquid product comprising liquified fermented *Houttuynia cordata* Thunb which is produced by heating green *Houttuynia cordata* Thunb to obtain a liquified Houttuynia, inoculating the liquified Houttuynia as culture medium with yeast, koji or a mixture thereof to ferment the inoculated liquified Houttuynia and then removing lees precipitated from said fermented liquified Houttuynia.

8. A liquid material according to claim 7, in which the culture medium includes a carbon source selected from the group consisting of saccharides, starch syrup, honey, starch, molasses and mixture thereof.

* * * * *